United States Patent [19]

Dawes

[11] 3,957,470

[45] May 18, 1976

[54] MOLECULE SEPARATORS

[76] Inventor: Ernest Fredrick Dawes, 99 Kilby Road, East Kew, Victoria, Australia

[22] Filed: Oct. 15, 1974

[21] Appl. No.: 514,810

[30] Foreign Application Priority Data
Oct. 18, 1973 Australia.............................. 5291/73

[52] U.S. Cl................................ 55/342; 29/157 R; 29/455 R; 55/17; 55/529; 65/36
[51] Int. Cl.².......................................... B01D 45/00
[58] Field of Search ........ 55/17, 342, 529, DIG. 14; 29/157 R, 455; 65/36

[56] References Cited
UNITED STATES PATENTS
2,607,439  8/1952  Dickens et al. ......................... 55/17
3,616,596  11/1971  Camparague .......................... 55/17
3,803,811  4/1974  Ryhage .............................. 55/17 X Primary Examiner—Frank W. Lutter
Assistant Examiner—Kathleen J. Prunner
Attorney, Agent, or Firm—Fleit & Jacobson

[57] ABSTRACT

A molecule separator comprising an evacuation chamber adapted to be connected to a vacuum pump, a pair of coaxially aligned input and output nozzles sealed within the chamber, the nozzles being formed of a single length of tubing having a transverse cut extending at least part way through the tubing so that the bore of the tubing communicates with the chamber, and means connecting the lengths of tubing on either side of the cut to maintain the cut sections of tubing in accurate axial alignment.

10 Claims, 7 Drawing Figures

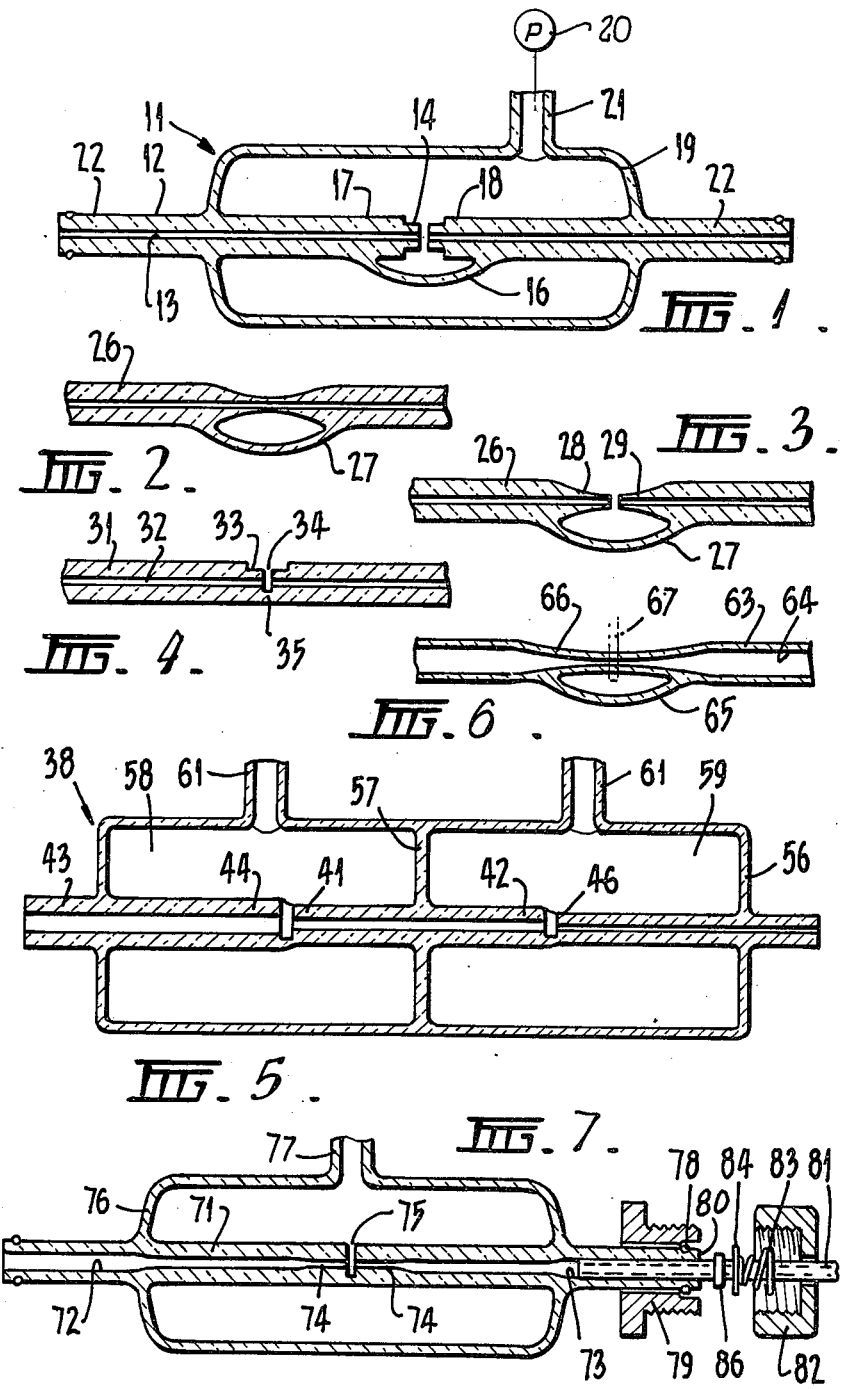

MOLECULE SEPARATORS

BACKGROUND OF THE INVENTION

This invention relates to an improved molecule separator and relates also to an improved method of making a molecule separator.

Molecule separators are typically used for separating a carrier gas from a specimen in gaseous form to be analysed by, for example, a mass spectrometer. The molecule separator is connected between the output of a gas chromatograph, for example, and the input of the ion source of the mass spectrometer. The separator may have one or more separating stages and in one commonly known construction, the separator consists of an evacuation chamber connected to a vacuum pump, a jet input nozzle arranged to be connected to the gas chromatograph and through which molecules in gas phase are supplied, and a coaxial output nozzle arranged to be connected to the analysing instrument.

The jets of the molecule separator are normally spaced apart a distance approximately 0.1 mm and they also generally have a diameter of about 0.1 mm, although it is not uncommon for the diameter of one jet — that is the output jet — to be larger than the input jet. Heretofor, it has been difficult to ensure completely accurate alignment of the jets in a molecule separator which is essential for the separator to function correctly.

SUMMARY OF THE INVENTION

It is an object of the present invention to provide an improved molecule separator having accurately aligned input and output jets.

A further object of the present invention is to provide an improved molecule separator which is relatively simple to manufacture and wherein the alignment of the jets is maintained during the life of the instrument.

A still further object of the invention is to provide an improved molecule separator which has a relatively high efficiency in separating the carrier gas, usually helium, from the specimen to be analysed.

A still further object of the invention is to provide an improved method of manufacturing a molecule separator.

According to the invention there is provided a molecule separator comprising an evacuation chamber, means to connect the evacuation chamber to a vacuum pump, and a pair of input and output nozzles coaxially aligned and sealed within the evacuation chamber, said input and output nozzles being formed of a single length of tubing having a transverse cut extending at least part way through the tubing so that the bore of the tubing communicates with the vacuum chamber, and means connecting the lengths of tubing on either side of the transverse cut.

According to another aspect of the invention there is provided a method of making a molecule separator which comprises the steps of making a transverse cut in a length of tubing, said cut extending at least through to the tubing bore, providing means on the tubing to maintain the tubing bore axially aligned after making the said transverse cut, sealing the tubing within an evacuation chamber, providing means on said evacuation chamber for connection to a vacuum pump, and providing input and output connections to said tubing in the evacuation chamber.

In the preferred form of the invention, the molecule separator is made of a length of glass tubing having a fine bore at least in the mid-section of the length of tubing. A transverse cut is made in the glass tubing through the fine bore section but not extending completely through the tube wall. Thus, part of the tube wall remains which acts as a mechanical support to maintain the cut sections of tubing accurately axially aligned. The length of tubing is sealed within a glass evacuation chamber which is provided with connection means to enable the molecule separator to be connected to a vacuum pump. The ends of the tubing assembly are connected to input and output tubes which are provided with means for attaching the molecule separator to a gas chromatograph or the like and an analysing instrument such as a mass spectrometer.

The molecule separator of the present invention may be made in two stages so that the output nozzle of the first stage communicates with an input nozzle of the second stage. The two stages may have jet diameters of identical dimensions or, alternatively, the jet diameters may vary by forming the two stages from a single length of tubing having three stepped bores. With such an arrangement the evacuation chamber surrounding the two stage nozzle construction is divided into two sections with each section having means for connection with evacuating means such as a vacuum pump to enable the first stage to be evacuated to a first pressure, such as to 0.001 mm Hg, and the second stage to be evacuated to a much reduced pressure.

The molecule separator according to the invention may be formed from fine bore glass or stainless steel tubing or tubing of other suitable material.

DESCRIPTION OF THE DRAWINGS

In order that the invention will be more readily understood several embodiments thereof will now be described with reference to the accompanying drawings wherein:

FIG. 1 is a cross-sectional elevational view of one form of molecule separator according to the invention;

FIGS. 2 and 3 are detail views illustrating a modified form of the separator nozzles before and after parting;

FIG. 4 illustrates a further construction of the separator nozzles;

FIG. 5 is a cross-sectional elevational view of a two stage molecule separator according to the invention;

FIG. 6 is a further detailed view illustrating the formation of another construction of separator nozzles, and FIG. 7 is a cross-sectional view of a further modified form of the invention.

Referring to FIG. 1 of the drawings, the molecule separator 11 is constructed of a length of glass tubing 12 having a fine bore 13 of approximately 0.2 mm. A circumferential groove 14 is ground on the tube 12 approximately mid-way along its length. The width and depth of the groove 14 are sufficient to provide a clearance around the subsequently formed nozzles to facilitate diffusion of the carrier gas away from the nozzle area.

After formation of the groove 14, a glass bridge 16 is fused to the tube 12 on each side of the groove 14. The bridge 16 rigidly supports both halves of the tube 12 when a cut is made transversely of the tube 12 substantially centrally of the groove 14 to form the spaced nozzles 17 and 18. The cut is of a width of approximately 0.3 mm.

The tube and bridge assembly is then mounted and sealed in a glass envelope 19 which is connected to vacuum pump 20 by connector tube 21. The ends 22 of the tube 12 extend beyond the end walls of the envelope 19 for connection to appropriate instruments in the manner known in the art.

As the nozzles 17 and 18 are formed by cutting the tube 12 after bridging the nozzle area the nozzle jets are accurately and permanently aligned.

Referring to FIGS. 2 and 3, the nozzles may be formed by firstly heating and necking the tube 26 to reduce the diameter of the tube 26 and its bore biameter. After necking down, a glass bridge 27 is fused to the tube 26 on both sides of the necked portion. A transverse cut is then made with a suitable cutting wheel through the necked portion to produce two aligned tapered nozzles 28 and 29. The necking operation is controlled to provide desired jet diameters of between approximately 0.1 mm and 0.2 mm. As in the previous embodiment, the bridge 27 mechanically supports the nozzles 28 and 29 in the aligned position.

The construction of nozzles shown in FIG. 4 obviates the necessity to provide a separate mechanical bridge. With this construction, the glass tube 31 having the fine bore 32 is ground to provide a groove 33 which extends only part way around the circumference of the tube 31, and is of a depth less than the tube wall thickness. A transverse cut 34 is then made in the tube 31 through the fine bore and centrally of the groove 33 but not extending completely through the tube wall. Thus, part 35 of the tube wall remains and provides a mechanical support to maintain the cut sections of tube accurately axially aligned. The width of the cut 34 is between 0.1 mm and 0.4 mm.

Referring to FIG. 5, the molecule separator 38 of this embodiment is a two stage separator with the output nozzle 41 of the first stage communicating directly with an input nozzle 42 of the second stage. The two stages each have jet diameters of decreasing size formed by constructing the nozzle of each stage from a single length of stepped tubing 43. With this arrangement, the input nozzles 44,42 of the respective stages are larger than the output 41,46 nozzles. The nozzles are produced by transverse cuts part way through the tube 43 at the step locations. The jet spacings are each 0.1 mm and the jet diameter is reduced from the first stage input jet diameter of 0.2 mm to a second stage output jet diameter of 0.1 mm. For each stage, the uncut portion of the tube 43 provides the necessary mechanical support for the nozzle to maintain the jets accurately aligned.

After formation of the nozzles the tube assembly is sealed inside a glass envelope 56 with sufficient of the ends of the tube 43 extending from the envelope 56 to enable connections to be made thereto. The envelope 56 contains a central annular wall 57 to divide the envelope 56 into the two evacuation chambers 58,59. Suitable connection tubes 61 are provided on each chamber for vacuum pumps to reduce the chamber pressures to operating pressures.

The embodiment illustrated in FIG. 6 shows the formation of a further arrangement of nozzles. The tube 63 has a relatively large diameter bore 64 which is reduced in size by appropriate necking 66 of the tube 63. Care is taken in reduction of the tube size not to substantially reduce the wall thickness. When the bore diameter is approximately 0.2 mm, a glass bridge 65 is fused to the tube 63 on both sides of the necking 66 and a transverse cut is made by a cutting blade 67 to form the separate jets with a spacing of 0.35 mm.

The embodiment of the invention illustrated in FIG. 7 comprises a glass tube 71 having inlet and outlet bores 72 and 73 of approximately 1.6 mm which reduce down to a jet bore 74 which is precision formed to 0.2 mm. A transverse cut 75 of 0.35 mm width is made part way through the tube 71 to form spaced jets. The uncut portion of the tube mechanically supports the jets in alignment. The tube 71 is sealed within a glass envelope 76 which has a vacuum pump connection tube 77. The ends of the tube 71 project beyond the ends of the envelope 76 and are provided with suitable connection means to enable the separator to be connected between, for example, a gas chromatograph and a mass spectrometer. The preferred connection means, one only of which is illustrated, comprises a stainless steel circlip 78 which engages in a circumferential groove in the tube end 80. A screw 79 is mounted on the tube end 80 and has an internal shoulder to engage the circlip 78.

The stainless steel tube or glass lined tube 81 to which the separator is connected has a threaded nut 82, and a tapered spring 83 which are arranged to engage with a washer 84 fixed to the tube 81. A seal 86 of polytetrafluoroethylene is disposed on the tube 81 between the washer 84 and the end of the tube end 80.

In a variation of this embodiment of the invention, the inlet jet diameter is 0.10 mm whilst the outlet jet diameter is 0.25 mm. The jets may be formed of one tube having a step down bore or they may be formed by aligning two separate tubes of different bore diameters and fusing the tubes together at the desired spacing of the tube ends.

I claim:

1. A molecule separator comprising an evacuation chamber, an evacuation means, means on the chamber for connecting said evacuating means to said chamber, a tube extending through the chamber and sealed to the chamber walls, said tube having a transverse cut at least part way therethrough to form two axially aligned nozzles in the chamber, the transverse cut passing through the bore of the tube, and rigid connecting means interconnecting the portions of tubing on both sides of the transverse cut.

2. A molecule separator according to claim 1 wherein said transverse cut extends part way through the tube, and said rigid connecting means comprises the uncut portion of the tube.

3. A molecule separator according to claim 2 wherein the bore diameter of each nozzle is less than the bore diameter of the remainder of the tube.

4. A molecule separator according to claim 1 wherein the bore diameter of one of the nozzles is greater than the bore diameter of the other of the nozzles.

5. A molecule separator according to claim 1 wherein said transverse cut extends completely through the tube and the rigid connecting means comprises a bridge connecting the tube on each side of the cut.

6. A molecule separator according to claim 5 wherein said nozzles are of tapered configuration.

7. A molecule separator according to claim 5 wherein the cross-section of the nozzles is reduced relative to the tube by circumferential grooving of the tube.

8. A molecule separator according to claim 1 wherein means are provided on the ends of the tube for connection with analysing apparatus, said means including a circumferential groove and circlip for engagement by tube joining and sealing means.

9. A molecule separator according to claim 1 wherein said evacuating chamber is divided into two sections, and a pair of axially aligned nozzles is provided in each section, the tubing sections on each side of each pair of nozzles being rigidly connected.

10. A method of making a molecule separator comprising the steps of making a transverse cut in a length of tubing having a bore, at least in the region of the cut, of between 0.05 mm and 0.3 mm, said cut having a width of between 0.05 mm and 0.4 mm and extending at least through to the tube bore, providing means on the tube to rigidly support the tube on both sides of the cut, sealing the tube ends to the walls of an evacuation chamber such that said cut is disposed within said chamber and said tube ends extend outwardly of said chamber, and providing means on the evacuation chamber for connecting the chamber to evacuating means.

* * * * *